(12) United States Patent
Main

(10) Patent No.: US 9,232,936 B2
(45) Date of Patent: Jan. 12, 2016

(54) RETRACTORS

(75) Inventor: David Main, Leeds (GB)

(73) Assignee: SURGICAL INNOVATIONS LIMITED, Leeds (GB)

( * ) Notice: Subject to any disclaimer, the term of this patent is extended or adjusted under 35 U.S.C. 154(b) by 51 days.

(21) Appl. No.: 13/582,078

(22) PCT Filed: Mar. 2, 2011

(86) PCT No.: PCT/GB2011/050416
§ 371 (c)(1), (2), (4) Date: Sep. 27, 2012

(87) PCT Pub. No.: WO2011/107800
PCT Pub. Date: Sep. 9, 2011

(65) Prior Publication Data
US 2013/0035554 A1 Feb. 7, 2013

(30) Foreign Application Priority Data
Mar. 3, 2010 (GB) .................................. 1003416.0

(51) Int. Cl.
*A61B 17/02* (2006.01)
*A61B 17/00* (2006.01)
(Continued)

(52) U.S. Cl.
CPC ....... *A61B 17/0218* (2013.01); *A61B 2017/003* (2013.01); *A61B 2017/00309* (2013.01); *A61B 2017/00314* (2013.01);
(Continued)

(58) Field of Classification Search
CPC ............... A61B 17/02; A61B 17/0218; A61B 17/0281; A61B 2017/0225; A61B 17/0206; A61B 1/32; A61B 1/005; A61B 1/0051; A61B 1/0052; A61B 1/0057; A61B 1/008

USPC ......... 600/201, 204, 208–213, 215, 216, 226, 600/235, 141, 142, 144–150
See application file for complete search history.

(56) References Cited

U.S. PATENT DOCUMENTS 5,284,128 A * 2/1994 Hart .............................. 600/208
5,308,342 A   5/1994 Sepetka et al.
(Continued)

FOREIGN PATENT DOCUMENTS

EP 0623004 B1 5/1997
GB 2456165 A 8/2009
(Continued)

OTHER PUBLICATIONS

International Search Report and Written Opinion for PCT/GB2011/050416 dated May 20, 2011.

*Primary Examiner* — Matthew Lawson
*Assistant Examiner* — Amy Sipp
(74) *Attorney, Agent, or Firm* — Shumaker, Loop & Kendrick, LLP

(57) ABSTRACT

A retractor having an elongate portion with first and second parts each with adjacent pivotally connected segments pivotable from a first configuration to a second configuration, wherein in the second configurations the adjacent segments abut each other to inhibit further movement, at least one of the parts including a control whereby a force required to move the first part from the first configuration towards the second configuration is less than the force required to move the second part from the first configuration towards the second configuration, and an actuator arranged to urge the first and second parts from the first to the second configurations at the same time.

9 Claims, 9 Drawing Sheets

(51) Int. Cl.
 *A61B 17/29* (2006.01)
 *A61B 17/32* (2006.01)

(52) U.S. Cl.
 CPC .......... *A61B 2017/00323* (2013.01); *A61B 2017/2908* (2013.01); *A61B 2017/320044* (2013.01); *Y10T 74/20006* (2015.01); *Y10T 74/20207* (2015.01)

(56) References Cited

U.S. PATENT DOCUMENTS

| | | | |
|---|---|---|---|
| 5,391,147 A * | 2/1995 | Imran | A61B 18/1492 600/434 |
| 5,441,483 A * | 8/1995 | Avitall | 604/95.05 |
| 5,467,763 A * | 11/1995 | McMahon et al. | 600/201 |
| 5,558,665 A * | 9/1996 | Kieturakis | 606/1 |
| 5,662,606 A * | 9/1997 | Cimino et al. | 604/95.04 |
| 6,002,955 A * | 12/1999 | Willems et al. | 600/374 |
| 6,705,989 B2 * | 3/2004 | Cuschieri et al. | 600/208 |
| 6,739,744 B2 * | 5/2004 | Williams et al. | 362/552 |
| 6,926,669 B1 * | 8/2005 | Stewart et al. | 600/439 |
| 7,713,190 B2 * | 5/2010 | Brock et al. | 600/114 |
| 7,854,109 B2 * | 12/2010 | Zubiate et al. | 59/78.1 |
| 8,092,479 B2 * | 1/2012 | Albrecht et al. | 606/191 |
| 8,388,520 B2 * | 3/2013 | Stefanchik et al. | 600/144 |
| 8,403,839 B2 * | 3/2013 | Roth et al. | 600/204 |
| 2004/0236316 A1 * | 11/2004 | Danitz et al. | 606/1 |
| 2005/0222601 A1 * | 10/2005 | Erhard | 606/190 |
| 2005/0288656 A1 * | 12/2005 | Koerner | A61B 18/02 606/21 |
| 2006/0122462 A1 * | 6/2006 | Roth et al. | 600/204 |
| 2006/0178562 A1 | 8/2006 | Saada et al. | |
| 2007/0118097 A1 * | 5/2007 | Miller | 606/1 |
| 2008/0051631 A1 * | 2/2008 | Dejima et al. | 600/114 |
| 2008/0091077 A1 * | 4/2008 | Roth et al. | 600/204 |
| 2008/0091079 A1 * | 4/2008 | Roth et al. | 600/205 |
| 2009/0079821 A1 * | 3/2009 | Bousquet et al. | 348/65 |
| 2009/0118621 A1 * | 5/2009 | Harhen | 600/466 |
| 2009/0299343 A1 * | 12/2009 | Rogers | 606/1 |
| 2010/0298636 A1 * | 11/2010 | Castro et al. | 600/104 |
| 2011/0257637 A1 * | 10/2011 | Timmerman | 606/1 |
| 2011/0295065 A1 * | 12/2011 | Gurusamy et al. | 600/114 |
| 2012/0253131 A1 * | 10/2012 | Malkowski et al. | 600/201 |
| 2013/0035554 A1 * | 2/2013 | Main | 600/206 |
| 2014/0018618 A1 * | 1/2014 | Mitelberg et al. | 600/104 |

FOREIGN PATENT DOCUMENTS

| | | | |
|---|---|---|---|
| WO | 9313713 | 7/1993 | |
| WO | WO 9313713 A1 * | 7/1993 | A61B 17/00 |
| WO | 01/23022 A1 | 4/2001 | |
| WO | 2007/089676 A1 | 8/2007 | |

* cited by examiner

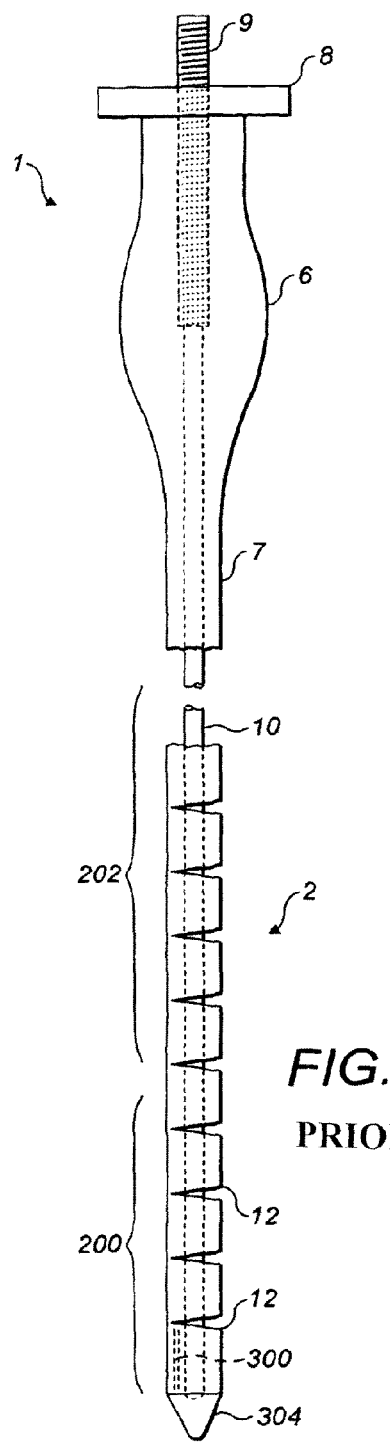
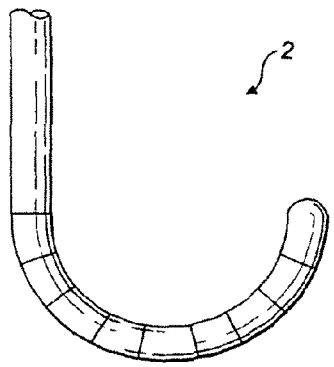
FIG. 2
PRIOR ART
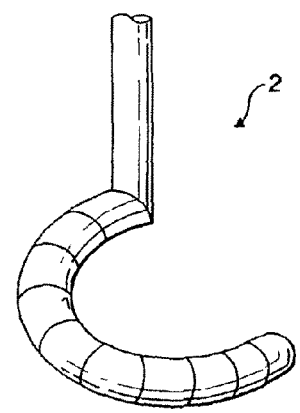
FIG. 3
PRIOR ART
FIG. 1
PRIOR ART
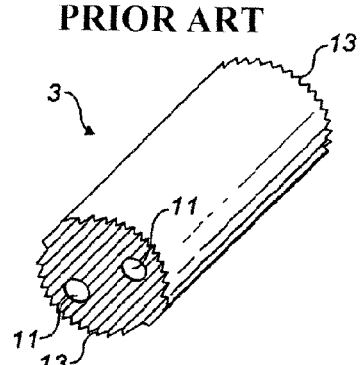
FIG. 4
PRIOR ART

RETRACTORS

CROSS REFERENCE TO RELATED APPLICATION

This application claims priority to PCT/GB2011/050416 filed Mar. 2, 2011, which claims priority to GB 1003516.0 filed Mar. 3, 2010, the entirety of each of which is incorporated by reference herein.

TECHNICAL FIELD AND BACKGROUND

The present invention relates to surgical instruments comprising retractors and a method of controlling such instruments. The invention is particularly applicable to endoscopic surgical instruments.

EP 0 623 004 discloses a surgical instrument comprising a retractor.

US2006/0178562 discloses methods and apparatus for obtaining endoluminal access comprising a steerable endoluminal guide having a variable pivot for altering steering dynamics.

US2009/0079821 discloses a steerable structure (21, 27) of the catheter or endoscope type, the structure comprising an elastically or deformable longitudinal body (22, 28) including at least one actuator (16, 38) of material of the shape memory type incorporated longitudinally with the body (22, 28) together with Joule-effect heater means enabling the actuator (16, 38) to be contracted longitudinally in order to cause the longitudinal body (22, 28) to bend.

U.S. Pat. No. 5,308,342 discloses a catheter composed of an outer coaxial tube or relatively high flexibility and three tandemly disclosed inner coaxial tube segments that vary in stiffness with the stiffest being located a the proximal end of the catheter and the least stiff ending proximal of the proximal end of the catheter.

GB 2 456 165 discloses a shaft 1 for an endoscopic instrument having two series of slots 5 and 6 forming a preferentially flexible portion 2. The series are offset and the length of the slots varies along at least one of the series to vary the flexibility of the shaft.

WO 01/23022 discloses an endoscope having an elongated flexible sheath (12), A first sleeve (20) has a passage (24) therethrough which snugly received the sheath (12), the first sheath (12) being slidable from its proximal end to its distal end.

BRIEF SUMMARY OF THE INVENTION

It is an object of the present invention to attempt to overcome at least one of the above or other disadvantages.

A surgical instrument comprising a retractor, the retractor including an elongate portion having a first part comprising adjacent pivotally connected segments pivotable from a first configuration to a second, different configuration and a second part comprising adjacent pivotally connected segments, at a different elongate extent along the elongate portion than the first part, pivotable from a first configuration to a second, different configuration in which, in the second configurations, the adjacent segments abut each other to inhibit further movement, at least one of the parts including a control whereby a force required to move the first part from the first configuration towards the second configuration is less than the force required to move the second part from the first configuration towards the second configuration and an actuator arranged to urge the first and second parts from the first to the second position at the same time.

According to one aspect of the present invention, an instrument, such as a surgical instrument for example, includes an elongate portion arranged, in use, to be inserted through a restricted opening into a body, the elongate portion being movable from a first configuration to a second, different configuration in which second configuration two parts of the instrument that are spaced from each other in the first configuration at least partially cross each other in second configuration.

The parts may contact each other in the second configuration.

The parts may completely cross each other in the second configuration and may completely cross each other such that the instrument extends over itself.

One of the parts may comprise an end region.

The parts may comprise parts that are spaced from the end region.

There may be at least two pairs of parts that are spaced from each other in the first configuration and at least partially cross each other, at different extents for the pairs, along the instrument in the second configuration, and going along the elongate extent of the instrument, the first pair may cross on one side of the instrument with the second pair also crossing on that side. There may be at least three pairs of parts that are spaced from each other in the first configuration and that at least partially cross each other at different extents, for the pairs, along the instrument in the second configuration and, going along the extent of the instrument, the first and second pairs may cross on the same side with the third pair crossing on the opposite side.

The end region may include a portion that is movable to extend up towards the location where the parts cross and down from the location where the parts cross.

The instrument may include a rigid portion, which rigid portion comprises at least one of the parts that at least partially cross each other and a plurality of parts that cross each other may include the rigid portion.

In the first configuration, the instrument extends in a common first direction and in which, in the second configuration part of the instrument extends in a second direction which is opposed to the first direction and in the second direction, the one part of the instrument may be caused to extend back towards another part. In the second configuration two spaced elongate extents of the instruments may both extend at an angle to the first direction.

The instrument may include spaced joint regions that enable the instrument to move from the first to the second configuration and the spaced joint regions may allow the instrument to cross itself at least twice in the second configuration. The joint regions may comprise a plurality of segments movable relative to each other to assist in causing the movement from the first to the second configurations.

The instrument may include first control means arranged to cause the movement from the first to the second configuration.

In the second configuration, the two parts may be biased towards each other at the region where they at least partially cross each other.

The instrument may include a flexible member extending outside of the instrument from the end region to a location spaced from the end region and the flexible member may be arranged to assist in effecting movement from the first to the second configuration and the flexible member may be arranged to be tensioned, initially, as movement from the first configuration commences and subsequently to be slackened. The instrument may include second control means arranged to control the operation of the flexible member. The first and second control means may be arranged to be coordinated to effect the movement from the first to the second configurations.

In the second configuration, one previously spaced part of the instrument may be arranged to be connected to another part of the instrument and one part may comprise the end portion of the instrument. The connection may be arranged to be by means of a plug and socket. The flexible member may be arranged to extend within the instrument and then out of the instrument in the region of where the parts are arranged to be connected and then to extend externally of the instrument to the other part that is to be connected whereby tensioning the flexible member is arranged to assist in effecting the connection.

According to another aspect of the present invention a method of controlling a surgical instrument comprises causing an elongate portion to move from a first configuration in which two parts are spaced from each other to a second configuration in which those parts at least partially cross each other.

The method may comprise causing the instrument to move to a second configuration in which the instrument crosses itself twice.

The present invention also includes a method of controlling an instrument when the instrument is as herein described.

According to one aspect of the present invention a surgical instrument includes an elongate portion arranged, in use, to be inserted through a restricted opening into a body, the elongate portion being movable from a first configuration to a second, different configuration in which second configuration two parts of the instrument that are spaced from each other in the first configuration at least partially cross each other in second configuration.

According to a further aspect of the present invention a method of controlling a surgical instrument comprises causing an elongate portion to move from a first configuration in which two parts are spaced from each other to a second configuration in which those parts at least partially cross each other.

The present invention also includes a method of performing surgery when using the instrument of the present invention or when controlling the instrument of the present invention.

The first configuration may be a straight configuration.

According to a further aspect of the present invention an instrument includes an elongate portion movable from a first configuration to a second, different configuration, the instrument including an operative member attached to the elongate portion at a first location and including an extent external to the elongate portion, the operative member, in use, being arranged to exert a force on the elongate portion to at least partially assist in causing the elongate portion to move at least part of the way between the first and second configurations.

According to a still further aspect of the present invention a method of operating an instrument includes an elongate portion and an operative member attached to the elongate portion, the operative member including an extent external to the elongate portion the method comprising exerting a force on the elongate portion thereby causing the elongate portion to move from the first configuration to a second, different configuration.

According to another aspect of the present invention an instrument includes an elongate portion movable from a first configuration to a second, different configuration, the elongate portion comprising a plurality of segments that are connected to each other by a connection means and that are movable relative to each other whereby the elongate portion can move from the first to the second configuration, the connection means comprising at least one pivot member acting as a hinge between the segments.

According to a further aspect of the present invention a method of connecting a plurality of segments of an elongate instrument such that the segments can move from a first configuration to a second, different configuration comprises using a pivot member to act as a hinge between the segments.

Any of the aspects of the invention may be combined.

The present invention is also defined in the claims.

BRIEF DESCRIPTION OF THE DRAWINGS

The present invention will be now be described, by way of example and with reference to the accompanying drawings, in which FIG. 1 is a side view of a surgical instrument comprising a surgical retractor 1 with an end 2 in a straight configuration;

FIG. 2 is a view of the end 2 of the retractor shown in FIG. 1 in a straight hook configuration;

FIG. 3 is a view of an end 2 of a retractor similar to that shown in FIG. 1 in an angled hook configuration, and FIG. 4 is a schematic perspective view of one of the segments 3 at the end 2 of the retractor shown in FIG. 1.

DETAILED DESCRIPTION OF THE INVENTION

Figure 5:
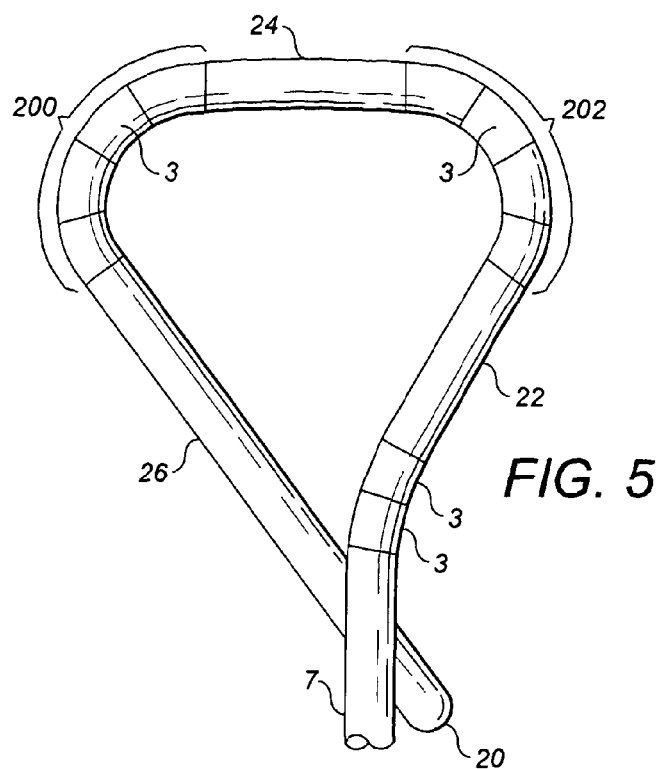
FIG. 5 is a front view of a first embodiment of a retractor.

FIG. 1 shows a retractor 1 having a handle 6 which is connected to the end 2 via a hollow rod (also referred to as elongate rigid rod) 7 and a first part 200 and a second part 202. In use, with the end in the configuration shown in the drawing, the end 2 and part of the rod 7 are fed through a tube in the abdominal wall. The surgeon is then able to manipulate the retractor by the handle 6 and change the configuration of the end 2 into the straight hook shape shown in FIG. 2 by rotating a knurled actuating nut 8.

The nut 8 is threadably connected to a screw member 9 whereby, when the nut 8 is rotated in a clockwise direction, looking from the free end of the handle, the screw member 9 is caused to move translationally away from the end 2. A loop of wire 10 is connected at its free ends to the member 9, and both sides of the loop pass through openings 11 in each segment 3. Accordingly as the wire 10 moves further into the rod 7 the segments are caused to tighten against each other.

As the segments 3 bear against each other they are caused to move out of the axial extent of the rod as the end faces 12 of each segment are formed at a slight angle to the perpendicular to the axis of the rod. In FIG. 1 the upwardly facing surfaces of each segment are parallel with each other as are the downwardly facing surfaces. Accordingly adjacent faces of the second part 202 and the first part 200 come into abutment with each other as the wire is tightened, and they take up the configuration shown in FIG. 2 in which a straight, substantially rigid hook which subtends approximately 180° is formed. Accordingly in the position shown in FIG. 1, each face extends at an angle of approximately 10° to the axis of the tube.

In order for the segments to take up the shape shown in FIG. 3, in which a substantially rigid hook which subtends approximately 180° in a direction generally at right angles to the axis of the rod, the face of at least one of the segments is angled differently. For instance, when the end 2 is in the relaxed position and extends generally in line with the axis of the rod 7, the uppermost segment faces the rod with a face extending at 45° to the axis of the rod, and the rod may be correspondingly angled at its end. Thus when the wire is tightened, the segment adjacent to the rod is caused to turn through 90°. The remaining upper and lower faces of the other segments may be parallel to each other in the configuration shown in FIG. 1 as previously described.

The hooks shown in FIGS. 2 and 3 can be used to displace or hold the organs in the required position.

To release the segments from the configuration shown in FIG. 2 or 3 the nut 8 is rotated in the opposite direction to release the tension in the wire. The wire is sufficiently strong, and the distance between the segments sufficiently small for the flexure of the wire to hold the segments generally straight for ease of insertion or removal when the hook configuration is not required. As the wire is threaded through two openings in each segment the strength of the wire and the close proximity of the segments prevents any significant relative turning of the segments around the longitudinal extent of the end 2.

The face of each segment which is caused to abut against another part of the retractor when in the hook configuration is formed with striations 13 which are parallel to each other and parallel to adjacent striations such that co-operating faces do not tend to slip in a rotational or translational sense.

With such retractors the remote end includes an exposed end 20. When pushing tissue aside this end can cause trauma to the body, particularly the liver. In addition there is inevitably some flexure in the segments. Such flexure causes the end section to have a reduced effect on pushing the liver.

Furthermore, whilst it is relatively easy to achieve the configuration shown it can be difficult to effect more complicated configurations.

Each of the embodiments of the retractors shown may be operated as described in relation to FIGS. 1 to 4. Accordingly only the differences will be described. In addition, each retractor is able to have a straight configuration to enable the retractor to be inserted or removed and only the second configurations are shown in which each adjacent segment abuts each other to inhibit further movement or bending.

In FIG. 5 there are four segments 3 (e.g., second part 202) adjacent to the hollow rod 7 and four at each of the further corners (e.g., first part 200). Long segments 22 and 24 extend between the short segments and a longer segment 26 has its tip 20 extending back under the rod 7. Ideally the tip 20 should be concealed in the view shown by the hollow rod.

This arrangement has advantages over the segmental arrangements shown in FIGS. 2 and 3 in that no twisting of the retractor about the shaft 7 occurs if the retractor is urged in a direction out of the plane shown or into the plane shown. In addition at least part of the tip 20 is concealed by the rod 7 or can trail the rod 7 thus effecting less trauma.

Figure 6:
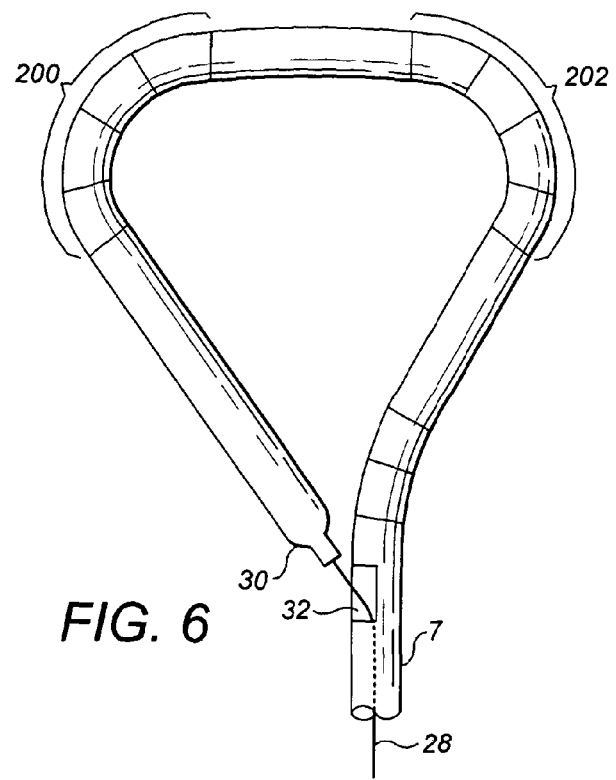
FIG. 6 is a front view of a second embodiment of a retractor.

FIG. 6 has the same general shape of that of FIG. 5. However the shaft 7 includes a further control cable 28 that is connected to the tip 30 of the elongate portion. The cable exits the shaft 7 just short of the first series of segments.

In use, either before the segments are tensioned by the wires 10 to take up the configuration shown, or after, or during at least part of that tensioning or any combination thereof the control cable 28 is tensioned to draw the tip 30 towards the shaft 7. A recess 32 may be provided in the shaft 7 in which the tip 30 may be drawn into and held by the cable.

This configuration allows greater force to be applied with less trauma being provided than that of FIG. 5. In addition the retractor can be urged in either direction to equal advantage as the configuration is symmetrical from the front and back.

Figure 7:
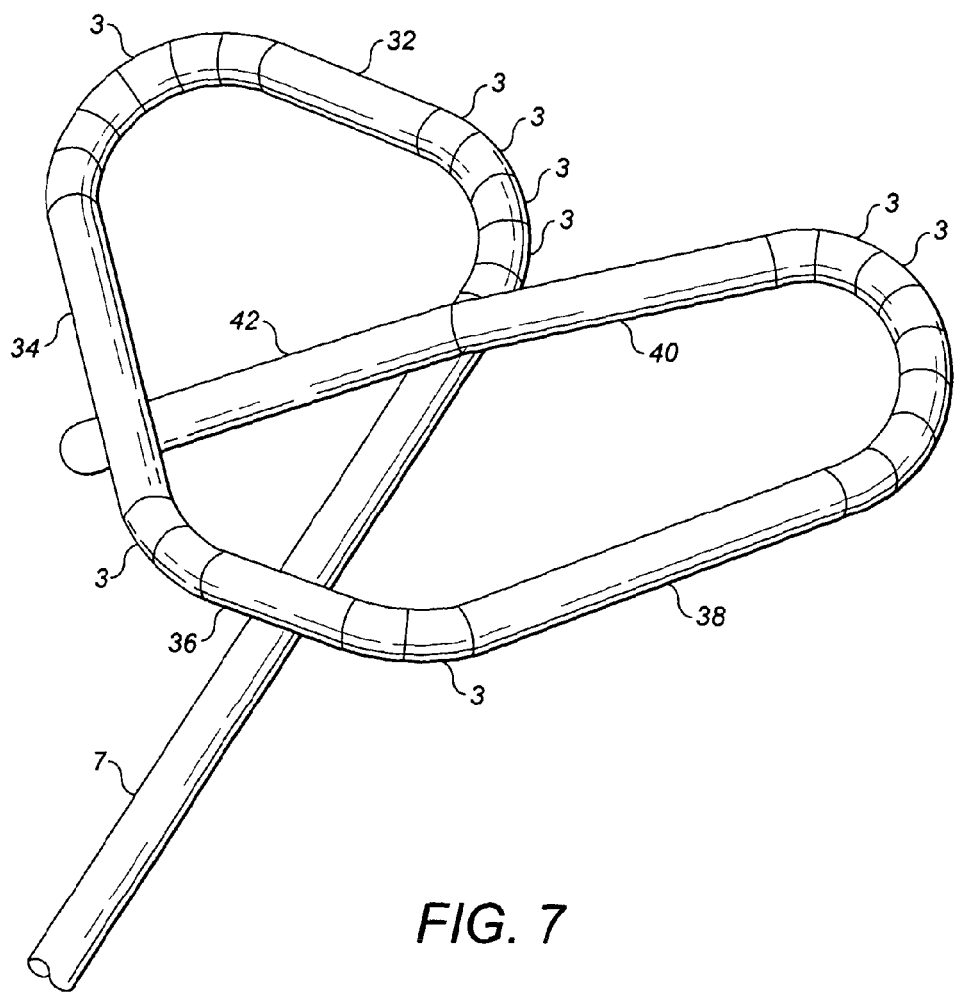
FIG. 7 is a perspective view of a third embodiment of a retractor.

Whilst the angles that the short segment of FIGS. 5 and 6 allow the retractor to turn are approximately 45°. 135° and 135° respectively the embodiment of FIG. 7 is more complicated.

In FIG. 7, starting from the rod 7, four short segments (an articulating joint) 3 allow the next long segment 32 to extend at 90° to the extent of the rod. Then six short segments (another articulating joint) 3 cause an even longer segment 34 to extend back towards the rod 7 at an angle of 45° to the rod. Then two short segments cause the "shortest" long segment 36 to cross over the rod 7, possibly in contact therewith, before two further short segments cause a further turn of 45° for the next long segment 38. Then eight short segments (yet another articulating joint) 3 cause a further turn of 180°. This brings two long segments 40 and 42 back over the rod 7 with the end of the segment 42 being tucked under the long segment 34. In certain aspects, 32, 34, 38, 40, and 42 may also be referred to as continuous, elongate linear segments.

The long segments 40 and 42 are connected by angled faces that allow the segment 40 to be inclined upwardly as it extends towards the rod with the segment 42 being inclined downwardly as it extends away from the rod (elongate rigid rod) 7. The movement of the segments 40 and 42 can be coordinated to take place as the end of the instrument moves back over the shaft towards the segment 34. Alternatively the segments 40 and 42 may be fixed together to form an angled suit such that they cannot move relative to each other. The segments 40 and 42 may be urged against the long segment 32 and the short segments 3 adjacent to the rod 7 as the segments 40 and 42 are being moved into place such that relative flexure of those parts occurs. When the joint between the segments 40 and 42 pass the segments 3 adjacent to the rod they spring back to allow the segment 42 to pass beneath the segment 34 and to maintain the shape shown under flexure with those parts crossing the rod being urged against the rod. Furthermore, that binding force may also cause the segment 36 to be biased. The biasing forces may be assisted by the angled slope of the segment 42 sliding along the segment 34 and pushing further against the segment 34 as the segment 42 slides further beneath the segment 34.

The configuration of FIG. 7 affords stability and strength in either direction. Furthermore trauma is reduced because of the considerable cross sectional area provided by the retractor or both sides of the shaft 7.

Although not shown in the drawing of FIG. 7, the end segment 42 may be connected to the shaft 7 by a control cable. The control cable may be tensioned to assist in the retractor leaving the straight configuration. As the wires tension the segments and as the retractor takes up the shape shown the cable may be tensioned or relaxed to assist in the shape being taken up.

As the retractor crosses the rigid rod in FIGS. 5 and 7 (and as the retractor is fixed in FIG. 6) when the rod is urged towards a liver with the cross parts being located between the rod and liver a rigid retractor is provided with a broad area of even force being applied.

FIGS. 8a-i are sequential views showing how the configuration of FIG. 7 is formed when the wire 10 is pulled. The first part of the instrument that bends is the proximal part between the rod 7 and the long segment 32 that changes shape from FIGS. 8a to 8b to 8c. When the short segments 3 abut each other to prevent further rotation at that location the adjacent short segments then cause the shape to change from FIGS. 8c to 8d. It can be seen that further tightening causes turning of the instrument to progress towards the proximal end possibly with abutment of distally located segment prior to adjacent proximal segments commencing to turn or possibly with a partial turn of distal segments prior to adjacent proximal segments commencing to turn.

It can be seen though that there is no control over how and when each segment commences to turn. Further, there is a large sweep when moving from FIGS. 8a to 8i, for instance, which may not be acceptable when using the instrument as a surgical retractor.

Figure 8D:
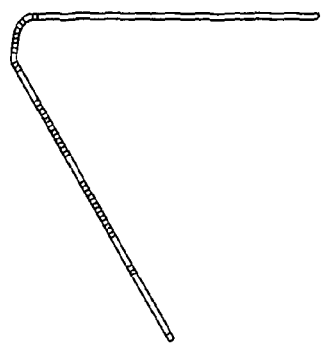
FIGS. 8a-i are sequential views showing how the configuration of FIG. 7 is formed when the wire 10 is pulled.
Figure 8C:
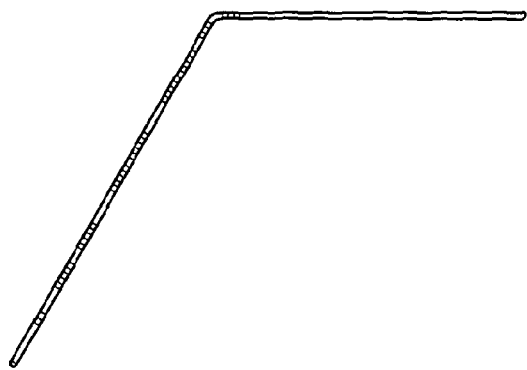
Figure 8B:
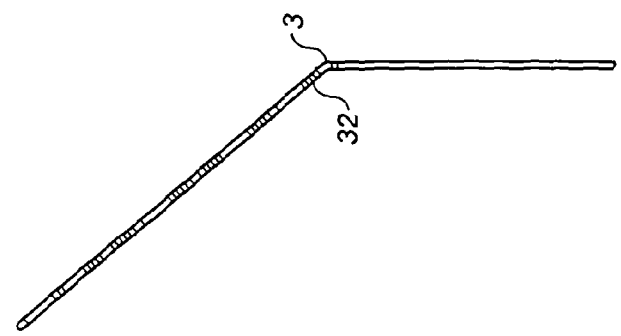
Figure 8A:
Figure 8I:
Figure 8H:
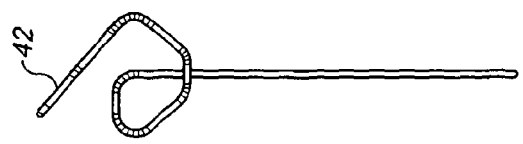
Figure 8G:
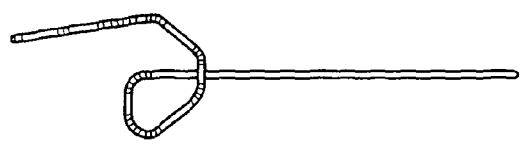
Figure 8F:
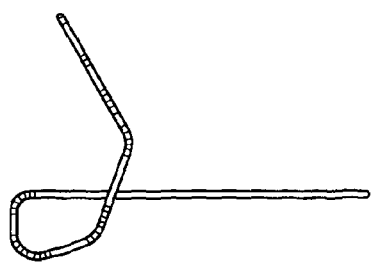
Figure 8E:
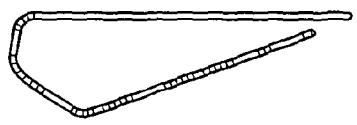

FIGS. 9a to i start and finish with the same configuration as that of FIGS. 8a and 8i when the wire 10 is progressively tightened. However the turning sequence is controlled. When the instrument is in the position shown in FIG. 9a, the force exerted on all segments urging them from the in line position may be equal.

Figure 9E:
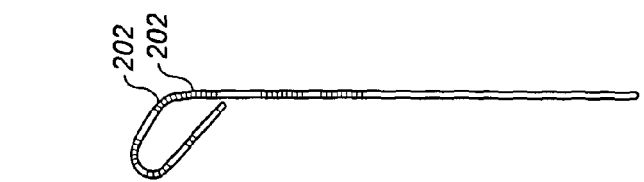
FIGS. 9a-j are sequential views showing how the configuration of FIG. 7 is formed when the wire 10 is pulled when using control members.
Figure 9D:
Figure 9C:
Figure 9B:
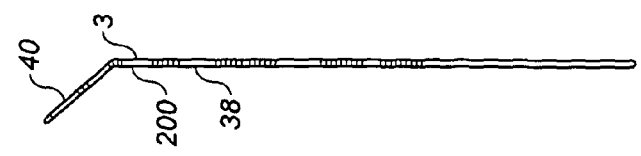
Figure 9A:
Figure 9J:
Figure 9I:
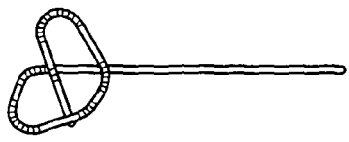
Figure 9H:
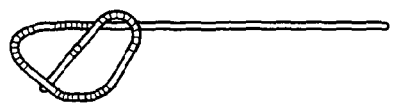
Figure 9G:
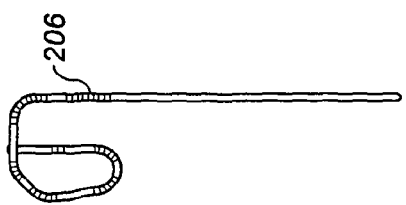
Figure 9F:
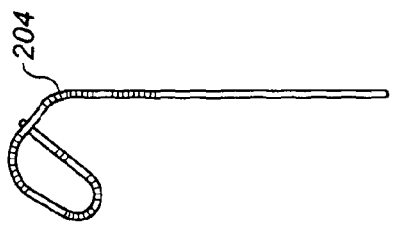

The first turn occurs at the distal end with the short segments 3 between the long segments 40 and 38 moving from the configuration of FIGS. 9a to 9d. When those segments 3 but each other or before abutment occurs the segments 3 between the long segment 38 and the long segment 36 start to turn to change the configuration from that of FIGS. 9d to 9e. Again when those segments 3 may abut each other or before they abut each other the adjacent distal segments start to turn. Such progressive successive turning of adjacent distal segments continues until the configuration of FIG. 9i is arrived at.

It can be seen that the change from FIGS. 9a to 9i involves only sweeping a very small area.

It will be appreciated that the individual control between adjacent segments that any sequence of progressive turning can be achieved.

Figure 10:
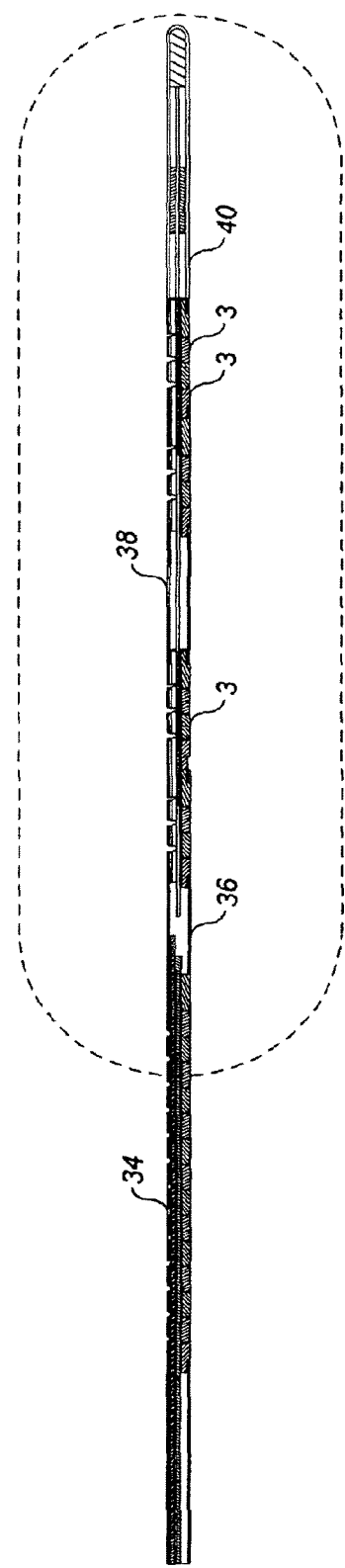
FIG. 10 is a longitudinal cross-section of the instrument that can form the shape of FIG. 7
Figure 11:
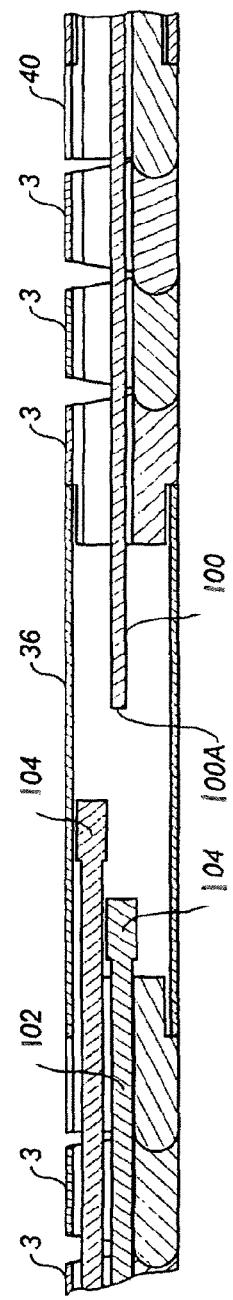
FIG. 11 is a detail of that figure.
Figure 12:
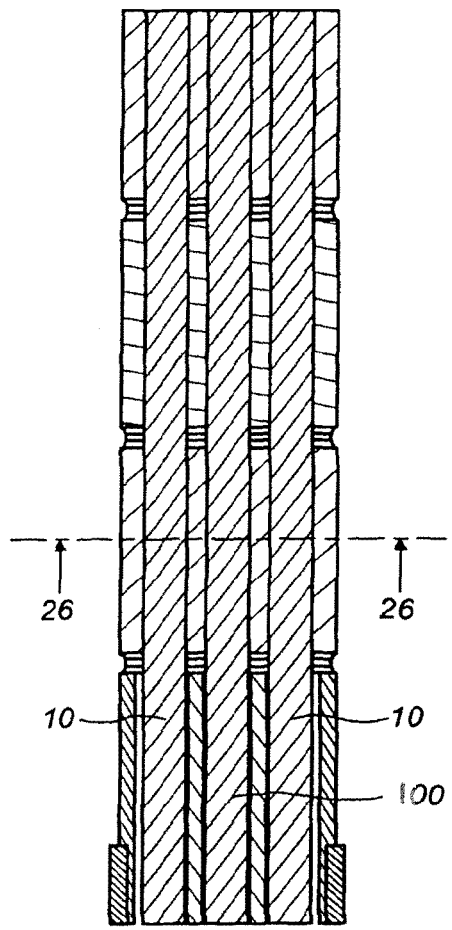
FIG. 12 is a longitudinal cross sectional view of part of the instrument showing the wire 10 and the control member and FIG. 13 is a cross-section of FIG. 12.

FIGS. 10 to 12 show how the control is applied. Long segments 34, 36, 38 and 40 are shown as in FIG. 7. However there may be a different number of short segments.

In FIGS. 10 and 11 the wire 10 that is pulled to turn the segments is not shown.

A control member 100 is connected to the end 40. The control member extends through the adjacent three segments 3 and has a free end 100A extending part of the way along segment 36. Further control members 102 extend from the long segment 36, through the segments 3, to the long segment 34. It will be appreciated that a control member may extend over the joint between two segments only or may extend across more than two segments. Furthermore, separate, spaced control members may be provided extending across the joints of different segments.

When the wire 10 is tightened to cause turning of the segments the control members 100 and 102 must also turn thus affording resistance to the turning (and also in due course assisting in the return of the segments to the configuration shown). The member 100 may be of the same material and/or may be of a slightly smaller diameter than each of the members 102. Accordingly the members 102 afford greater resistance to turning and the distal segments between the long segments 36 and 40 will start to turn first. Each control member may slide relation to part of the segments when these segments turn and may be stationary relative to one part of the segments. This is because the control members are one offset from the pivotal axis of the segments.

Either when all of the segments with the member 100 extending therethrough abut each other or shortly before that, the segments 3 with the members 102 extending through them will start to turn, overcoming the resistance afforded by the members 102.

Only one end of the members 102 is shown. They may be provided at each end with enlarged heads 104. This stops the members 102 from moving out of the segments that they control. It also allows for the members to be straight and curved without the heads abutting the segments to restrict turning as the distance between the heads at each end is greater than the distance that they occupy when the segments are at their limit of turning. Abutment of the segments may limit the extent of a turn. Alternatively or additionally abutment of the heads 104 at each end of one or both members 102 with segments at the end of a portion that is being controlled may limit the extent of a turn. As the member or members may be offset relative to the pivot axis of the segments, relative sliding between the member or members and the segments may occur.

The control members comprise spring steel or a memory metal such as NiTiNoL which may comprise Ni:Ti 50:50 Nickel Titanium alloy. Whilst the members 100 and 102 are shown as being of the same or similar diameter and material they may be of different material. Alternatively they may be of different cross sectional dimensions such as of different diameters. Alternatively the members 102 may be connected along their length.

Figure 13:
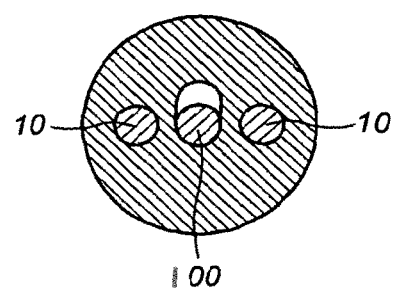

FIGS. 12 and 13 show the location of the wire 10 and the control member 100.

Referring back now to FIGS. 9a to g, the resistance of the control member or members 100, 102, 104, and 106 progressively increases. However, if desired, the control members could be arranged in an order such that 100 affords the greatest resistance, then 104, then 102 and then 106 or, indeed, any sequence of turning may be effected by varying the location of the control members. In this manner the sequence of movement of any bendable member can be controlled.

Similarly in FIGS. 5 and 6 the control member 100 may afford less resistance than the control member 102.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A surgical instrument comprising an elongate retractor having a handle connected to an elongate rigid rod,
   a plurality of continuous, elongate linear segments positioned along the retractor,
   at least two articulating joints positioned along the retractor such that the articulating joints interconnect the elongate rigid rod and the plurality of continuous, elongate linear segments, each articulating joint further comprising a plurality of asymmetrical segments when viewed in cross section that are positioned uniformly along the retractor and are movable relative to one another and the plurality of continuous, elongate linear segments;
   a control that is a stiffening member configured to control movement of the articulating joints and continuous, elongate linear segments; and
   an actuator arranged separately from the control, wherein:
   a first and a second articulating joint of the at least two articulating joints having at least one of the plurality of continuous, elongate linear segment positioned therebetween such that the first and second articulating joints are spaced apart relative to each other along the elongate retractor;
   the first articulating joint being positioned closer to the handle than the second articulating joint and the second articulating joint being positioned closer to a distal end of the surgical instrument than the first articulating joint;
   the stiffening member comprises a plurality of elongate wires positioned internally along a longitudinal axis of the surgical instrument in which an end of a first elongate wire of the plurality of elongate wires has a larger diameter than an end of a second elongate wire of the plurality of elongate wires;
   the end of the first elongate wire of the plurality of elongate wires is configured to contact the end of the second elongate wire of the plurality of elongate wires to move the surgical instrument;
   the stiffening member and the plurality of asymmetrical segments are configured to work in concert to restrict movement of the surgical instrument such that only a predetermined range of movement is achieved by moving the surgical instrument from a first configuration to a second configuration; and
   the plurality of elongate wires proximal the first articulating joint affords a greater resistance to pivotal motion than the plurality of elongate wires proximal the second articulating joint such that the second articulating joint is configured to pivotably move before the first articulating joint from the first configuration to the second configuration, wherein the second configuration is pretzel shaped.

2. The instrument as claimed in claim 1 in which the control is located in a central region of the articulating joints.

3. The instrument as claimed in claim 1 wherein the control is made of metal.

4. The instrument as claimed in claim 1 in which the control is arranged to assist in returning the surgical instrument from the second configuration towards the first configuration.

5. The instrument as claimed in claim 1 in which the plurality of continuous, elongate linear segments is at least three continuous, elongate linear segments being interconnected by articulating joints, and
   the articulating joint closest to the distal end of the surgical instrument is configured to pivotably move before the other articulating joints.

6. The instrument as claimed in claim 1 in which the actuator is arranged to exert an equal bias on at least one of the plurality of continuous, elongate linear segments and at least one articulating joint to urge them away from the first configuration.

7. The instrument as claimed in claim 1 in which the actuator comprises at least one wire extending along the length of at least one of the plurality of continuous, elongate linear segments, wherein the wire is arranged to be tightened to effect movement from the first to the second configuration.

8. The instrument as claimed in claim 1 in which an internal gap exists between at least one of the plurality of continuous, elongate linear segments and an adjacent articulating joint having separate controls positioned on opposite sides of the gap such that ends of the separate controls are configured to be advanced and retracted relative to one another when moving from the first configuration towards the second configuration or vice versa.

9. A method of using a surgical instrument comprising:
   moving a second articulating joint closest to a distal end of the surgical instrument relative to a handle of the surgical instrument from a first configuration to a second configuration before moving a first articulating joint that is closer to the handle of the surgical instrument, wherein:
   the surgical instrument comprises an elongate retractor having the handle connected to an elongate rigid rod,
   a plurality of continuous, elongate linear segments positioned along the retractor,
   at least two articulating joints positioned along the retractor such that the articulating joints interconnect the elongate rigid rod and the plurality of continuous, elongate linear segments, each articulating joint further comprising a plurality of asymmetrical segments when viewed in cross section that are positioned uniformly along the retractor and are movable relative to one another and the plurality of continuous, elongate linear segments; wherein the at least two articulating joints comprise the first and second articulating joints;
   a control that is a stiffening member for controlling movement of the articulating joints and continuous, elongate linear segments; and
   an actuator arranged separately from the control, wherein:
   the first and second articulating joints have at least one of the plurality of continuous, elongate linear segments positioned therebetween such that the first and second articulating joints are spaced apart relative to each other along the elongate retractor;
   the first articulating joint being positioned closer to the handle than the second articulating joint and the second articulating joint being positioned closer to the distal end of the surgical instrument than the first articulating joint;
   the stiffening member comprises a plurality of elongate wires positioned internally along a longitudinal axis of the surgical instrument in which an end of a first elongate wire of the plurality of elongate wires has a larger diameter than an end of a second elongate wire of the plurality of elongate wires;
   the end of the first elongate wire of the plurality of elongate wires is configured to contact the end of the second elongate wire of the plurality of elongate wires to move the surgical instrument;
   the stiffening member and the plurality of asymmetrical segments are configured to work in concert to restrict movement of the surgical instrument such that only a predetermined range of movement is achieved by moving the surgical instrument from a first configuration to a second configuration; and the plurality of elongate wires proximal the first articulating joint affords a greater resistance to pivotal motion than the plurality of elongate wires proximal the second articulating joint such that the second articulating joint is configured to pivotably move before the first articulating joint from the first configuration to the second configuration, wherein the second configuration is pretzel shaped.

* * * * *